United States Patent [19]

Grace et al.

[11] Patent Number: 5,049,861
[45] Date of Patent: Sep. 17, 1991

[54] METHOD AND SYSTEM FOR DETECTING UNDERGROUND MINE FIRES

[75] Inventors: Richard Grace; Alberto M. Guzman, both of Pittsburgh; David A. Purta, Gibsonia, all of Pa.

[73] Assignee: American Intell-Sensors Corp., Pittsburgh, Pa.

[21] Appl. No.: 532,892

[22] Filed: Jun. 1, 1990

[51] Int. Cl.$^5$ .............................................. G08B 17/10
[52] U.S. Cl. ................................... 340/632; 73/23.31
[58] Field of Search .............. 340/632, 633, 634, 603; 73/23.2, 23.31

[56] References Cited

PUBLICATIONS

Safety in Mines Research, edited by Dai Guoquan, Nov. 1987.
Early fire detection using trace gases in the airstream, Eicker, 1988.
Merits of CO and $CO/CO_2$ ratios for fire detection in diesel operated mines, Litton.
Early Warning Fire Detection Using Low Level Carbon Monoxide Monitors, Miller, 8-1978.

Primary Examiner—Donnie L. Crosland
Assistant Examiner—Jeffrey A. Hofsass
Attorney, Agent, or Firm—Reed Smith Shaw & McClay

[57] ABSTRACT

A CO based, Diesel discriminating, fire detection system and method is disclosed which significantly reduces the threshold of CO needed to detect a fire in a mine that also contains CO from Diesel equipment without a corresponding increase in the number of false alarms. The system measures both the CO and NO levels at many points throughout the mine and calculates a CO/NO ratio for each of these locations. A long term average concentration (4 hours) and a short term average concentration (1 hour) for both CO and NO are continually updated to reflect the changing dynamics of the mine environment. Using the CO/NO ratio, the detection system can effectively differentiate between CO produced by a Diesel and CO produced from a fire and can activate an alarm when the CO level resulting from a fire exceeds a predetermined threshold level.

13 Claims, 2 Drawing Sheets

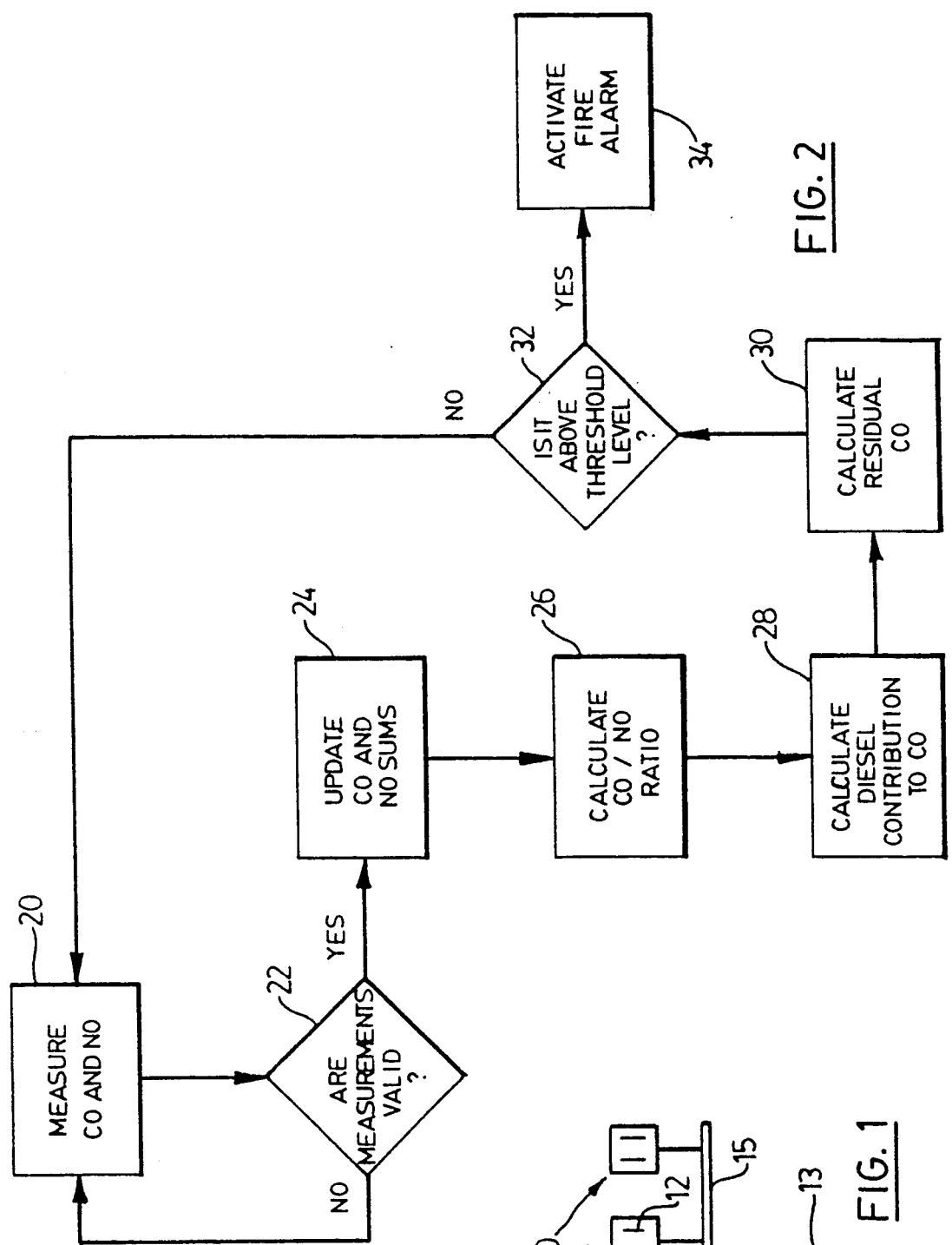

METHOD AND SYSTEM FOR DETECTING UNDERGROUND MINE FIRES

FIELD OF THE INVENTION

The present invention relates to a method and system for detecting the changes in the concentration of various gases in an underground mine to provide an early warning fire detection system.

BACKGROUND OF THE INVENTION

The fire detection systems presently use many mines throughout the world are based only on the detection of carbon monoxide ("CO"). See "Proceedings of the 22nd International Conference of Safety in Mines Research Institutes," and particularly the article by W. Heyn and K. Holke entitled "Testing of Fire Detection Systems for the Early Detection of Fires in the Underground Belt Conveyor Road", Nov., 1987, at pp 515-520. Studies conducted by the U.S. Bureau of Mines show that CO is generated by fires and in mines can be used to detect them in the early stages of development since very small quantities of CO can be measured with present day sensors. For example, the studies show that the CO emanating from a smoldering fire rises over a period of about 8 minutes from 0 to 35 ppm. Thereafter, flames appear and the CO generated from the fire rises very rapidly.

The CO based fire detection systems typically send an alarm signal at a threshold of 10 to 15 ppm above the minimal ambient background levels. Although these detection systems, in many cases, are quite reliable, they have not been used with much success in mines where Diesel powered equipment is also operated. The problem is that the engine's exhaust of Diesel powered equipment contains CO which is misinterpreted by the detection system as a fire resulting in many false alarms. These false alarms severely reduce the utility of these CO based fire detection systems in mines using Diesel powered equipment since the alarm threshold level must be set so high to reduce the number of false alarms that the sensitivity and early warning capability provided by the system is greatly reduced.

Other fire detection systems also take into account other gases which may be present in a mine such as $H_2$, $CO_2$, NO, $CH_4$ and other hydrocarbons. See Eicker, "Early Fire Detection Using Trace Gases in the Airstream", Gluckauf and Translation 124 (1988) Nr. 10 at pp. 304-309. The problem with this approach is that it either requires the monitoring of a large number of gases or the use of expensive and complicated equipment such as a gas chromatograph.

Recently, the U.S. Bureau of Mines contemplated the development of a fire detection system that used the ratio of CO to oxides of nitrogen ($NO_x$). See U.S. Bureau of Mines Information (Internal Report) entitled "The Merits of CO and $CO/CO_2$ Ratios for Fire Detection In Diesel Operated Mines" by C. D. Litton. This proposed system is based on the fact that a Diesel engine produces both CO and NO, whereas a smoldering fire produces only CO. It also assumes that all Diesel engines produce CO and NO in a predictable and fixed ratio. The disadvantage with this proposed approach is that it assumes that all Diesel engines produce CO and NO at a predictable and fixed rate. Experimental results have determined that the CO and $NO_x$ levels in a mine are not predictable and do not maintain a fixed ratio. Rather, they are dynamic and change over time, varying from mine to mine and even from point to point within a given mine.

It would be desirable, therefore, to have a method and system for detecting fires in an underground mine using a CO based detection system which did not have the above-described disadvantages.

SUMMARY OF THE INVENTION

Generally, the present invention provides a system for detecting underground mine fires comprising a plurality of sensor pairs located throughout the mine that are electrically connected to a data processor which processes the signals from the sensor pairs and determines if a fire is occurring. Preferably, the sensor pairs are connected to a single bus which is connected to a central computer to reduce the amount of wiring needed throughout the mine. A sensor pair comprises a first sensor for detecting the CO level located in very close proximity to a second sensor for detecting one of the oxides of nitrogen (i.e. $NO_x$ where x is an integer greater than zero but less than 4). Preferably, the sensor detects the level of NO since this is the most common oxide of nitrogen in a mine and the one that is produced in large quantities by Diesel engines, however, $NO_2$ or $NO_3$ could also be used. Any type of gas sensor can be used which can selectively measure CO or $NO_x$. Such sensors include electrochemical, semiconductor or catalytic.

The detection system of the present invention operates by measuring the CO and NO levels at each sensor pair and calculating the CO/NO ratio. Alternatively, it could calculate the NO/CO ratio. The data processor continually updates the CO/NO ratio for each sensor pair based on the most recent measurements from that pair. The CO/NO ratio is then used to distinguish the CO produced by Diesel engines from that produced by a fire. In this way the fire detection system can take into account changes and variations in the CO and NO levels throughout the mine caused by the use of Diesel engines in various parts of the mine. As a result, the system can effectively monitor the small CO concentration due to an early fire, even in the presence of a substantial background amount of CO from Diesel engines. The use of the CO/NO ratio enables the detection system to minimize the Diesel related false alarms experienced by CO only type systems while not compromising the sensitivity of the fire detection system.

In the method of the present invention, the current CO and NO level is measured at each sensor pair. A criteria is then applied to these measurements to determine if they are valid and can be used. For example, a zero NO value should not be used to determine the ratio. Typically, the measurements should be within a predetermined range which is programmed in the computer.

If the measurements are valid they are used to update a short term concentration level and a long term concentration level for both CO and NO. The two levels are sums of the concentrations over a specified period of time and are used together to monitor the correlation between the CO and NO concentrations at the various locations in the mine.

The measurements at each sensor pair can be made as often as one would like. Presently, each sensor pair is sampled every six seconds, but only every tenth sample is sent to the data processor which preferably is a central computer or microprocessor. Once the long term and short term levels of CO and NO have been updated with the most recent valid measurement, the CO/NO ratio is calculated for both the long term level and the short term level. These ratios are then used with the most recent NO measurement to obtain an estimate of the contribution to the measured CO level from the Diesel engines for both the short term and long term level. The smaller of these two numbers is then subtracted from the current CO measurement to obtain the current value of residual CO. If the residual CO is higher than a preset level, then an alarm is activated signalling the presence of a fire.

In a preferred embodiment of the present invention a weighted sum of the CO and NO levels is used rather than a straight average to calculate the short term concentration level, preferably calculated over the last one hour, and the long term concentration level, preferably calculated over the last four hours. These concentration level sums are exponentially weighted so that the more recent measurements are given greater weight. One benefit of this approach is that it requires less memory space in the data processor. This is significant when one considers that there may be several hundred sensor pairs in a mine. Also, to improve the reliability in the present invention, a confidence variable is calculated for the long term and short term concentration levels before the CO/NO ratio is calculated for each one. A benefit of this approach is that the system will gradually turn itself off if it does not receive valid data and will gradually turn on as it receives more valid data, based on the value of the calculated confidence variable. The confidence variable is used when the Diesel contribution to the CO level is calculated.

Other details, objects and advantages of the present invention will become apparent as the following description of the presently preferred embodiment of practicing the invention proceeds.

BRIEF DESCRIPTION OF THE DRAWINGS

In the accompanying drawings, preferred embodiments of the present invention are illustrated wherein:

FIG. 1 is a block diagram of the fire detection system of the present invention;

FIG. 2 is a block diagram of the method of the present invention; and

DETAILED DESCRIPTION OF THE INVENTION

Figure 3:
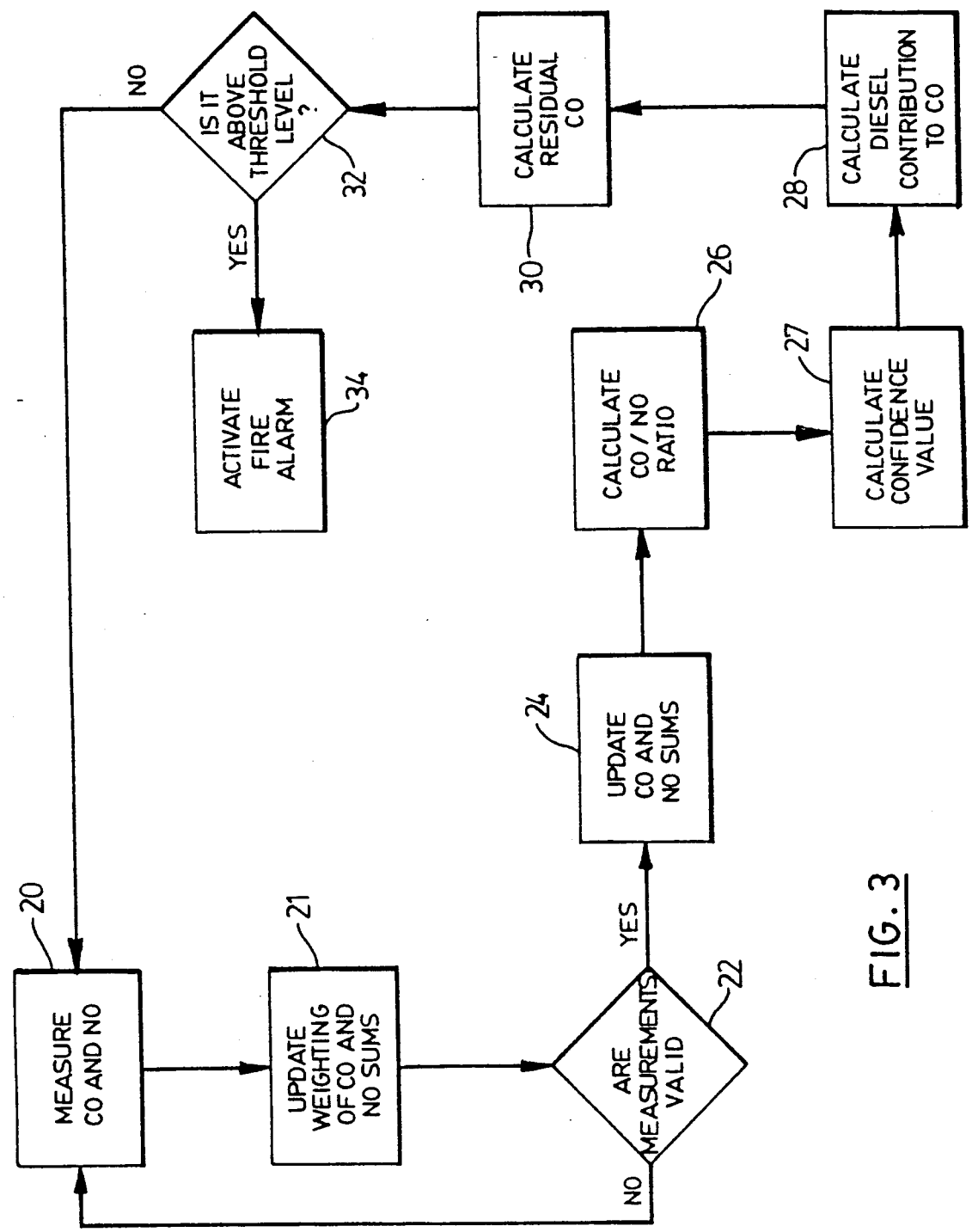
FIG. 3 is a block diagram of a preferred embodiment of the method of the present invention.

As shown in FIG. 1, the fire detection system preferably comprises: a plurality of remote sensor units 10 mounted throughout a mine that contain a pair of commercially available sensors for detecting CO and NO such as electrochemical cells; a data processor 13, preferably comprising a central computer or microprocessor; and a communications network 14, preferably comprising a bus 15 for transmitting the sensor readings to the data processor 13. The sensors 11 and 12 in each pair are located in close proximity to one another, preferably within six inches and are periodically read, preferably every minute, and the data is sent to the data processor 13 where the data is interpreted to separate the measured CO concentration into two parts. The two parts are: (a) a main contribution from Diesel engines, and (b) a residual contribution which includes the non Diesel background, if any, and the contribution from a smoldering fire, if present. This separation of the measured CO is accomplished by exploiting a correlation between the CO and NO found in Diesel exhaust.

The method used by the present system determines the most applicable CO/NO ratio by continuously considering CO and NO measurements over a sliding period of time. When the CO/NO ratio is decreasing, effectively reducing the sensitivity of the system, the method is designed to quickly track the CO/NO ratio using the short term concentration to minimize the effect of reducing sensitivity. When the CO/NO ratio, is increasing, the method is designed to calculate the CO/NO ratio using the long term concentration so that an increase in the CO/NO ratio due to a fire will not be tracked. The system accomplishes these goals by using two time scales for calculating the average CO/NO ratio. Preferably a one hour time period is used for the short term concentration to calculate the average CO/NO ratio when the CO/NO ratio is decreasing over time. The use of the one hour time scale is sufficient to obtain a meaningful measurement of the CO/NO ratio but still short enough so that the system will not be in a state of decreased sensitivity for long periods of time. Preferably a four hour time period is used for the long term concentration when the CO/NO ratio is increasing over time. The four hour period ensures that CO from a smoldering fire will not be tracked by the calculated CO/NO ratio. Other time periods, however, can be used.

The system when first activated must collect data for a period of time before a reliable calculation of the CO/NO ratio can be made. Conversely, if data is missing for a long period of time or if the CO and NO levels become very low, the reliability of the calculation is reduced. This situation is dealt with by calculating a confidence variable that is related to the availability of data from the sensor pairs 11 and 12 over the time periods in questions. The confidence variable which changes smoothly between zero and one is used to slowly turn the system on and off based on the availability of valid data. This insures that the system will not make corrections based on insufficient information.

As shown in FIG. 2, the first step 20 of the method of the present invention is to measure the most recent value of the CO and NO concentration at each sensor pair 11 and 12. This measurement occurs at a time interval $\Delta t$ from the previous measurement. Preferably, $\Delta t$ is between 30 and 60 seconds. The CO measurement is made by the first electrochemical sensor 11 in the sensor pair and the NO measurement is made by the second electrochemical sensor in the sensor pair.

In step 22, a criteria is applied to the measured data to determine if it is valid. Any number of different criteria could be used by those skilled in the art. For example, the data must be a positive number and preferably above a preset level. If the data is not valid, a counter is updated in the central processing unit 13 and at the next $\Delta t$ another CO and NO measurement is taken at each sensor pair. If the data is valid, the CO and NO measurements are added in step 24 to the long term and short term concentration sums for each of these gases for each sensor pair. In step 26, the average CO/NO ratio (represented by $\alpha_i$) is calculated using the sums obtained in step 24 for both the long term concentration ($\alpha_4$), and the short term concentration ($\alpha_1$). In step 28, the current Diesel contribution to the total measured CO is calculated using the following equation:

$$CO_{Di} = \alpha_i \cdot NO$$

where $CO_D$ is the calculated Diesel contribution to the carbon monoxide level and NO is the most recent valid measurement of the oxide of nitrogen being measured. The subscript i can be a 1 or a 4 to indicate that these calculations are performed for both the short term concentration average and the long term concentration average. Although the time frames of 1 hour and 4 hours have been used in the present invention, it is clear that other time frames may be used with varying amounts of accuracy.

In step 30, the residual CO (represented by $CO_R$) is calculated for each sensor pair for both the long term concentration and the short term concentration using the following equation:

$$CO_{Ri} = CO - CO_{Di}$$

where CO is the most recent valid measurement from a sensor pair. The system then chooses the largest of the two residual CO concentrations (from between the long tern and short term) to be used for fire detection. Thus:

$$Co_R = CO_{R1}, \text{ when } CO_{R1} \geq CO_{R4}$$

or $$CO_R = CO_{R4}, \text{ when } CO_{R1} < CO_{R4}$$

If the residual CO is above a predetermined value, an alarm will be activated in step 34 to indicate the presence of a fire. Selecting the maximum of the two residual values ensures that the system will track more quickly for a falling value of $\alpha_i$ and more slowly for a rising value of $\alpha_i$ thereby maintaining the sensitivity of the system when $\alpha_i$ is decreasing and not tracking the CO evolution of a possible fire when $\alpha_i$ is increasing.

FIG. 3 shows a preferred embodiment of the present invention which is similar to FIG. 2 except that several enhancements have been added which increase the sensitivity and reliability of the invention. For example, a new step 21, has been added which updates the value of the sums of the CO and NO concentrations for each sensor pair, by applying a weighting factor to these values. In that way, the more recent measurements can be emphasized while the importance of the older measurements is reduced. In one example, the weighting that is used is:

$$W_1 = (1 - \Delta t / \tau_1)$$

and $$W_4 = (1 - \Delta t / \tau_4)$$

where $\tau_1$ equals 1 hour, $\tau_4$ equals 4 hours and $\Delta t$ equals 1 minute. In general it is preferred that $\Delta t$ is small compared to $\tau_1$ and $\tau_4$. This weighting is then applied to the various sum quantities for each sensor pair.

Another improvement has been added in step 27. Preferably in this step, a confidence variable is calculated which is then used in calculating the Diesel contribution to the measured CO. This confidence variable enables the correction for the Diesel CO to be turned on and off smoothly based on the amount of valid data measured by the system. A simple confidence variable is the number of valid measurements divided by the total number of measurements. Another confidence variable $C_i$ that can be used is:

$$C_i = 1/\tau_i \sum_{j=1}^{n} W_i^{(n-j)} = (1/\tau_i) \cdot N_i$$

where j is summed from 1, the first measurement, to n, the current measurement, $W_i$ is the weighting factor, $N_1$ is the summation of the weighting factors $W_1$ and $\tau_i$ is the exponential time constant. Using this equation, approximately 3 time constant periods are necessary to obtain 95% confidence in the system output. This confidence variable is then multiplied by the Diesel contribution $CO_{Di}$ in step 28 before the residual CO concentration is calculated. Thus $$CO_{Ri} = CO - (C_i \cdot CO_{Di})$$

A prototype system has recently been tested in an actual mine. This mine already had a commercial fire detection system utilizing the standard CO only sensors. One sensor unit 10 containing a pair of sensors 11 and 12 was installed at a location where false alarms from Diesel engine exhaust has been a problem. The sensor unit was connected to the existing communications network and data collection system in the mine. The sensor unit collected data for an extended period of time. Once every minute the data was collected, stored and sent to a computer for processing and analysis. The correlation between the CO and NO in the data was generally good indicating that the large CO peaks detected can be identified as being from Diesel exhaust. Another approach to obtain an even more accurate measurement would be to integrate or average the data from each sensor over a sampling period of 30-60 seconds.

For a typical day, the two ratios $\alpha_1$ and $\alpha_4$ fluctuate around a mean value of about 4. As expected, $\alpha_1$ responds faster to changes in the CO/NO ratio and has larger fluctuations in amplitude. The short and long term confidence variables, $C_1$ and $C_4$, associated with $\alpha_1$ and $\alpha_4$, respectively, both approach 1 exponentially with time constants of 1 and 4 hours, respectively. These values are used to smoothly turn on the calculation making sure the system has received sufficient valid information upon which to base the determinations. Initially, when the system is first activated, the residual CO is seen to track the measured CO. After few hours, the correction due to $C_i$ is completely turned on and the peaks in the residual CO are very much reduced from the measured CO peaks. Indeed, the preliminary test data for a particular date indicates that a threshold of 15 ppm would have resulted in no false alarms while a threshold of 40 ppm would be needed if only the measured CO was used in order to produce no false alarms. This data also indicates that the residual CO tends to fluctuate by 1-2 ppm around zero.

The present fire detection system can significantly reduce the thresholds needed to detect a fire in a mine that contains Diesel equipment while not causing a significant number of false alarms. Based on the test data collected on the prototype system it is possible to upgrade a CO fire detection system to a CO/NO Diesel discriminating fire detection system which will operate with a threshold that is reduced by a factor of two to three, giving far superior fire detection ability, while largely reducing the number of false alarms.

While a presently preferred embodiment of practicing the invention has been shown and described with particularity in connection with the accompanying drawings, the invention may be otherwise embodied within the scope of the following claims.

What is claimed is:

1. A fire detection system for detecting underground mine fires comprising a plurality of remotely located sensor pairs, one sensor in each pair capable of measuring the Co concentration and the other sensor capable of measuring the $NO_x$ concentration; a data processor; and a communications network for periodically transmitting the measured CO and $NO_x$ concentration levels at the sensors to the data processor; wherein a dynamic $CO/NO_x$ ratio is calculated by the data processor using a variable number of measurements, said variable number dependant upon a particular sensed condition and is sued to determine the presence of a fire.

2. The entire system as described in claim 1 wherein the dynamic $CO/NO_x$ ratio is used by the data processor to calculate a residual CO concentration.

3. The system as described in claim 2 wherein the dynamic $CO/NO_x$ ratio is used by the data processor to calculate a Diesel contribution to the measured CO which in turn is used to calculate the residual CO concentration.

4. The system as described in claim 3 wherein an alarm is activated when the residual CO is above a predetermined level.

5. The system as described in claim 4 wherein $NO_x = NO$.

6. A method of detecting the presence of a mine fire comprising the steps of:

(a) measuring NO and CO concentrations at a sensor pair;

(b) updating a long term and a short term sum of the CO concentration and the NO concentration measured by the sensor;

(c) calculating a CO/NO ratio for the long term concentration and a CO/NO ratio for the short term concentration;

(d) selecting the smaller of the two CO/NO ratios calculated in step (c);

(e) calculating a residual CO concentration from the smaller CO/NO ratio; and (f) activating an alarm if the residual CO concentration exceeds a predetermined level.

7. The method as described in claim 6 wherein step (e) further comprises using the smaller CO/NO ratio to calculate a Diesel contribution to the measured CO and wherein the residual CO concentration is determined by subtracting the Diesel contribution from the measured CO.

8. The method as described in claim 7 further comprising calculating a confidence variable $C_i$ and multiplying the Diesel contribution by $C_i$ before determining the residual CO concentration.

9. The method as described in claim 8 wherein $C_i$ equals the number of valid measurements divided by the total number of measurements.

10. The method as described in claim 6 wherein the long term and short term average of the CO concentration and the NO concentration comprise a weighted average.

11. The method as described in claim 10, wherein the weighting factor $W_1$ is calculated using the equation $W_1 = (1 - \Delta t/\tau_1)$ where $\Delta t$ is a time interval from a previous measurement and $\tau_1$ is an exponential time constant.

12. The method as described in claim 11 further comprising calculating a confidence variable $C_i$ and multiplying the Diesel contribution by $C_i$ before determining the residual CO concentration.

13. The method as described in claim 12 wherein $C_1$ is calculated using the equation $C_1 = N_1/\tau_i$ where $N_i$ is the summation of weighting factors $W_i$.

* * * * *

UNITED STATES PATENT AND TRADEMARK OFFICE
CERTIFICATE OF CORRECTION

PATENT NO. : 5,049,861
DATED : September 17, 1991
INVENTOR(S) : Richard Grace, et. al.

It is certified that error appears in the above-indentified patent and that said Letters Patent is hereby corrected as shown below:

In Column 6, line 7, please delete "$N_1$" and "$W_1$" and insert therefor -- $N_i$ -- and -- $W_i$ --.

In Column 8, line 28, please delete "$W_1$" and insert therefor -- $W_i$ --.

In Column 8, line 29, please delete "$W_1$" and "$r_1$" and insert therefor -- $W_i$ -- and -- $r_i$ --.

In Column 8, line 36, please delete "$C_1$" and insert therefor -- $C_i$ --.

In Column 8, line 37, please delete "$C_1$" and "$N_1$" and insert therefor -- $C_i$ -- and -- $N_i$ --.

Signed and Sealed this

Nineteenth Day of October, 1993

BRUCE LEHMAN

*Attest:*

*Attesting Officer*          *Commissioner of Patents and Trademarks*